United States Patent
Hillshafer et al.

(10) Patent No.: US 9,487,467 B2
(45) Date of Patent: Nov. 8, 2016

(54) METHOD FOR PRODUCING o-PHTHALATE POLYESTER POLYOLS WITH LOW CYCLIC ESTER CONTENT

(75) Inventors: Douglas Hillshafer, Western Springs, IL (US); Andrew Guo, Wilmette, IL (US)

(73) Assignee: Stepan Company, Northfield, IL (US)

( * ) Notice: Subject to any disclaimer, the term of this patent is extended or adjusted under 35 U.S.C. 154(b) by 376 days.

(21) Appl. No.: 14/004,887

(22) PCT Filed: Mar. 7, 2012

(86) PCT No.: PCT/US2012/027932
§ 371 (c)(1),
(2), (4) Date: Oct. 1, 2013

(87) PCT Pub. No.: WO2012/125353
PCT Pub. Date: Sep. 20, 2012

(65) Prior Publication Data
US 2014/0018458 A1   Jan. 16, 2014

Related U.S. Application Data

(60) Provisional application No. 61/453,429, filed on Mar. 16, 2011.

(51) Int. Cl.
| | | |
|---|---|---|
| *C07C 67/08* | (2006.01) | |
| *C08G 18/08* | (2006.01) | |
| *C08G 18/34* | (2006.01) | |
| *C08G 18/42* | (2006.01) | |
| *C08G 63/181* | (2006.01) | |
| *C09D 175/06* | (2006.01) | |
| *C09J 175/06* | (2006.01) | |

(52) U.S. Cl.
CPC ............ *C07C 67/08* (2013.01); *C08G 18/14* (2013.01); *C08G 18/341* (2013.01); *C08G 18/4211* (2013.01); *C08G 18/4252* (2013.01); *C08G 63/181* (2013.01); *C09D 175/06* (2013.01); *C09J 175/06* (2013.01)

(58) Field of Classification Search
CPC ... C07C 67/08; C08G 18/14; C08G 18/4211; C08G 18/4252; C08G 63/181; C08G 18/341; C09D 175/06; C09J 175/06
See application file for complete search history.

(56) References Cited

U.S. PATENT DOCUMENTS

| | | | |
|---|---|---|---|
| 2,092,031 A | 9/1937 | Spanagel et al. | |
| 3,431,279 A * | 3/1969 | Ehrhart | C07D 323/00 524/108 |
| 3,457,236 A * | 7/1969 | Ehrhart | C08G 63/181 526/68 |
| 6,515,080 B1 | 2/2003 | Wiegner et al. | |
| 6,569,352 B1 | 5/2003 | Hillshafer et al. | |
| 2005/0032925 A1 | 2/2005 | Kaplan | |
| 2006/0035994 A1 | 2/2006 | Kaplan | |
| 2006/0175575 A1 | 8/2006 | Kaplan | |
| 2010/0210757 A1 | 8/2010 | Sommer et al. | |
| 2010/0240785 A1* | 9/2010 | Hickey | C08G 18/36 521/157 |

FOREIGN PATENT DOCUMENTS

| | | |
|---|---|---|
| CA | 2189836 | 6/2004 |
| CA | 2687360 A1 | 11/2008 |
| EP | 1035145 | 9/2000 |
| EP | 1074597 | 2/2001 |
| EP | 2496616 | 9/2012 |

OTHER PUBLICATIONS

Ehrhart, J. Org. Chem. 33 1968, 2930.

* cited by examiner

*Primary Examiner* — Rabon Sergent
(74) *Attorney, Agent, or Firm* — Dilworth IP LLC

(57) ABSTRACT

A method for producing a polyester polyol is disclosed. The method comprises reacting phthalic anhydride with a diol selected from the group consisting of ethylene glycol, propylene glycol, 1,3-propanediol, 2-methyl-1,3-propanediol, neopentyl glycol, 1,6-hexanediol, polyethylene glycols having a number average molecular weight within the range of 200 g/mol to 600 g/mol, and mixtures thereof at a diol to phthalic anhydride molar ratio within the range of 1.1 to 1.6. The resulting o-phthalate polyester polyol has a hydroxyl value in the range of 18 to 400 mg KOH/g, an acid value in the range of 0.2 to 5.0 mg KOH/g, and 1 wt. % or less of cyclic esters.

14 Claims, No Drawings

METHOD FOR PRODUCING o-PHTHALATE POLYESTER POLYOLS WITH LOW CYCLIC ESTER CONTENT

FIELD OF THE INVENTION

The invention relates to polyester polyols, particularly to polyols based on phthalic anhydride that have a low content of cyclic esters.

BACKGROUND OF THE INVENTION

Polyester polyols are hydroxy-functional condensation polymers made by reacting aliphatic or aromatic di- or polycarboxylic acids with polyols (usually diols). Polyester polyols react with polyisocyanates, chain extenders, and other components to produce polyurethanes for foams, coatings, adhesives, sealants, elastomers, and other applications. For example, polyester polyols based on aliphatic diacids are commonly used to make polyurethane elastomers for shoe soles.

Polyester polyols based on aromatic diacids and their derivatives, most notably terephthalic acid, isophthalic acid, and phthalic anhydride are well known. Aromatic diacids impart mechanical strength, thermal stability, chemical resistance, and other attributes to products made from their polyester polyols. Some aromatic polyester polyols are particularly valuable for making, e.g., flexible packaging adhesives or rigid foams for insulation or automotive instrument panels. For many polyester polyol applications, phthalic anhydride is the aromatic "diacid" of choice because of its low cost, ease of formulation, and low tendency to have precipitates compared with either terephthalic acid or isophthalic acid.

For end-use applications in which there may be indirect contact of the polyurethane with food (e.g., an adhesive used to bond layers of packaging film), formulators and regulators have redoubled efforts to identify and limit or eliminate traces of by-products having a tendency to migrate. For instance, by-products that lack hydroxyl functionality but are present in a polyester polyol (e.g., a cyclic ester) will not react with polyisocyanates to form a high polymer. Consequently, these by-products could migrate from the ultimate polyurethane adhesive.

In o-phthalate-based polyester polyols, cyclic esters are potentially generated by self-condensation of an o-phthalate monoester. The tendency to cyclize should depend on the nature of the diol reactant (chain length, branching, and other factors), but the degree to which such cyclic esters will form in a process designed to make the polyester is generally not well understood. Numerous references (e.g., U.S. Pat. No. 6,569,352) teach the preparation of phthalic anhydride-based polyester polyols, but these references do not recognize the issue of cyclic ester formation arising from the use of certain diols. Thus, for instance, DEG and 1,4-butanediol are typically taught as the equivalent of EG.

Ehrhart (*J. Org. Chem.* 33 (1968) 2930) showed that macrocyclic o-phthalate esters can be generated by thermolyzing the corresponding polyester polyol. In particular, the o-phthalate polyesters of diethylene, triethylene, 1,5-pentylene, and 1,6-hexylene glycols can be converted nearly quantitatively to the respective macrocycle, while other glycols, including ethylene glycol, give poorer yields of the macrocycle. The amount of cyclic ester present in the polyester polyol prior to thermolysis was not determined. U.S. Pat. No. 2,092,031 also reports making the macrocycle from phthalic anhydride and ethylene glycol by depolymerizing the corresponding polyester polyol (see Table 1).

U.S. Pat. No. 6,515,080 teaches a process for making polyethylene terephthalate modified with o-phthalate units. A pre-condensate of phthalic anhydride and ethylene glycol is made using a 2-3.5 molar excess of ethylene glycol. As shown in Table 1 of the '080 patent, condensation polymerization of phthalic anhydride and ethylene glycol can produce about 3 wt. % of the corresponding cyclic ester (mol. wt.=192 g/mol), although this cyclic ester was apparently not seen in a similar experiment (Table 2).

A variety of polyester polyols based on phthalic anhydride and diethylene glycol (DEG) are valuable commercial products for urethane coatings, adhesives, sealants, and elastomers. Examples include Stepanpol® PS and PD series polyols such as Stepanpol PS-20-200A, PS-1752, PD-110 LV, PD-200 LV, and PD-56. Despite its utility in polyester polyols, DEG may eventually become scarce because of a trend in the chemical industry favoring production of "ethylene glycol only" instead of its mixture with DEG, triethylene glycol, and higher glycols.

Our own recent work, outlined below, indicates that cyclic esters (typically about 3-8%) are produced in the production of polyester polyols, particularly when DEG, 1,4-butanediol, and other common glycols are reacted with phthalic anhydride. However, for reasons discussed earlier, it is often desirable to make polyester polyols, particularly o-phthalate polyester polyols intended for CASE applications, with very low levels of cyclic esters.

SUMMARY OF THE INVENTION

In one aspect, the invention relates to method for making a polyester polyol. The method comprises reacting phthalic anhydride with a particular diol or diol mixture at a diol to phthalic anhydride molar ratio within the range of 1.1 to 1.6. The diol is selected from the group consisting of ethylene glycol, propylene glycol, 1,3-propanediol, 2-methyl-1,3-propanediol, neopentyl glycol, 1,6-hexanediol, polyethylene glycols having a number average molecular weight within the range of 200 g/mol to 600 g/mol, and mixtures thereof. The resulting o-phthalate polyester polyol has a hydroxyl value in the range of 18 to 400 mg KOH/g, an acid value in the range of 0.2 to 5.0 mg KOH/g, and 1 wt. % or less of cyclic esters. The invention includes polyurethanes made using polyester polyols produced according to the inventive method.

DETAILED DESCRIPTION OF THE INVENTION

The inventive method reacts phthalic anhydride and a diol to make a polyester polyol. Phthalic anhydride is commercially available from many suppliers, including Stepan Company (Northfield, Ill.), and any desired form (e.g., flake, molten) can be used. Smaller quantities can be obtained from Sigma-Aldrich and similar suppliers. The purity of phthalic anhydride is not considered critical for the inventive method. Preferably, however, the phthalic anhydride is at least 95% pure, more preferably at least 98% pure.

Diol selection is an important aspect of the inventive method. In particular, the diol is selected from the group consisting of ethylene glycol, propylene glycol, 1,3-propanediol, 2-methyl-1,3-propanediol, neopentyl glycol, 1,6-hexanediol, polyethylene glycols having a number average molecular weight within the range of 200 g/mol to 600 g/mol, and mixtures thereof. All of these diols are commercially available. We surprisingly found that the amount of cyclic esters generated in the reaction of diols with phthalic anhydride is not easily predicted from the expected ring size of a 1:1 cyclic adduct (see Tables 1 and 2, below). For instance, we found that in the preparation of a 300-320 hydroxyl value polyester polyol based on phthalic anhydride, a relatively high proportion (>2%) of cyclic ester is generated when the diol is 1,4-butanediol, diethylene glycol, triethylene glycol, or tripropylene glycol, but not when the diol is ethylene glycol, 1,3-propanediol, 1,6-hexanediol, or PEG-400. (As used herein, "%," when used to describe an amount of cyclic ester, unless specifically noted as "wt. %," refers to an area % integrated using GPC software.)

In a preferred aspect, the phthalic anhydride (PA) is reacted with ethylene glycol, a polyethylene glycol having a number average molecular weight within the range of 200 g/mol to 600 g/mol, or a mixture thereof. When ethylene glycol (EG) is used, the source is not critical, and it need not be of high purity. However, EG containing a large proportion (e.g., 5-10 wt. % or more) of DEG and/or triethylene glycol should be avoided to prevent making a polyester polyol having more than 1 wt. % of cyclic esters. Surprisingly, a polyester polyol having a very low content of cyclic esters can be made with EG as the only diol. We found, for instance, that polyester polyols having hydroxyl values from 56-320 mg KOH/g and 0.2 to 1% of cyclic esters could be made from EG alone (see Table 1, below).

Using a diol or diol mixture having a molecular weight less than that of DEG (e.g., EG, 1,3-propanediol, or the like, or a mixture thereof) is desirable when a high PA content (e.g., greater than 50 wt. %) is desired in the polyester polyol. Compared with polyols made from phthalic anhydride and DEG, such polyols can provide increased adhesion, although combination with a natural oil (as described below) will usually be needed to achieve an acceptably low viscosity.

The polyethylene glycol (PEG), when used, has a number average molecular weight ($M_n$) within the range of 200 g/mol to 600 g/mol, preferably from 250 g/mol to 400 g/mol. When the $M_n$ is below 200, the PEG has a tendency to form cyclic esters when reacted with phthalic anhydride. On the other hand, PEGs having number average molecular weights greater than 600 g/mol are generally undesirable because the molecular weight of the polyester polyol becomes greater than is desirable, while coincidentally, the hydroxyl concentration becomes undesirably low.

In a preferred aspect of the inventive method, ethylene glycol and at least one polyethylene glycol are reacted with the phthalic anhydride to make the polyester polyol. By using a mixture of EG and a polyethylene glycol having a number average molecular weight from 200 to 600 g/mol, the polyol manufacturer can strike a favorable balance between the desired degree of hard segment (i.e., with a higher proportion of EG) and the degree of flexibility or hydrophilicity (i.e., with a higher proportion of PEG). This balance is achieved while avoiding cyclic ester contents greater than 1 wt. % in the polyester polyol because neither the EG nor the PEG used generates a high proportion of cyclic esters. Including PEG in the formulation can also help to keep viscosity within desirable limits or give a liquid product.

In another preferred aspect, the molar ratio of ethylene glycol to polyethylene glycol is within the range of 0.2 to 3.0, more preferably from 0.3 to 2.5.

In a particularly preferred aspect, a polyethylene glycol having $M_n$=400 g/mol or its mixture with EG is used to make the polyester polyol. As shown in Examples 7-9 below (Table 1), polyester polyols having hydroxyl values in the 56-200 mg KOH/g range and no detectable amount of cyclic esters can be made with PEG-400 alone or in combination with 50 mole % EG.

The diol and phthalic anhydride are reacted at a diol to phthalic anhydride molar ratio within the range of 1.1 to 1.6. Excess diol is used to ensure essentially complete conversion of the phthalic anhydride to esterified products and little or no remaining carboxylic acid functionality. Preferably, the diol to phthalic anhydride molar ratio is within the range of 1.1 to 1.4, most preferably about 1.3.

The esterification of phthalic anhydride and the diol can be performed at any desired temperature that provides an acceptable reaction time (typically, several hours to one day). When EG is the only diol, the temperature may be somewhat lower than usual because EG has a boiling point of about 195° C. Generally, the esterification will be performed at a temperature within the range of 130° C. to 260° C., more preferably from 160° C. to 230° C. It is most convenient, but not necessary, to esterify at atmospheric pressure. An oxygen-free atmosphere (nitrogen, argon, or the like) is preferably used to prevent discoloration of the polyol.

The process can be performed with or without an esterification catalyst. When a catalyst is used, it is often added during the later stages of the esterification to reduce the temperature needed to drive the reaction to completion. Preferred esterification catalysts comprise titanium. Tetra (alkoxy)titanium compounds, such as tetra(n-butoxy)titanium or tetra(i-propoxy)titanium, are particularly preferred.

o-Phthalate polyester polyols made using the inventive method have a hydroxyl value within the range of 18 to 400 mg KOH/g, preferably from 56 to 320 mg KOH/g. At hydroxyl values below 18, the reactivity of the polyols with polyisocyanates to form urethanes is normally too low, while hydroxyl values greater than 400 can cause reactivity to be too high or undermine urethane flexibility and tensile properties. Hydroxyl value can be measured by any suitable technique, such as ASTM E 222. Conveniently, hydroxyl value is determined by reacting accurately weighed samples with an excess amount of acetylating agent, hydrolyzing excess reagent, and titrating with standardized NaOH or KOH to measure the amount of acetic acid present. A suitable method for determining the hydroxyl value of polyester polyols made by the inventive method appears below.

The o-phthalate polyester polyol has an acid value within the range of 0.2 to 5.0 mg KOH/g, more typically from 0.5 to 3.0 mg KOH/g. Thus, it is not crucial for all of the acidity to be eliminated, but a high degree of residual acidity should be avoided. Acid value can be measured by any convenient method, such as ASTM D4662 or the like. In one suitable approach, accurately weighed samples are dissolved in acetone, isopropyl alcohol, or another suitable solvent, and the mixture is titrated with standardized aqueous NaOH or KOH. A suitable method for determining the acid value of polyester polyols made by the inventive method appears below.

o-Phthalate polyester polyols made by the inventive method comprise 1 wt. % or less, preferably 0.5 wt. % or less, and more preferably 0.2 wt. % or less of cyclic esters. By "cyclic ester," we mean the macrocyclic diester(s) made by condensing the carboxy groups of phthalic anhydride with the hydroxyl groups at opposite ends a diol molecule.

The amount of cyclic ester present in the polyester polyol can be determined by any desired analytical method. In one convenient approach, samples are analyzed by gel permeation chromatography under conditions that permit separation of the cyclic ester from any residual diol. One suitable GPC technique that utilizes UV detection at 254 nm is particularly effective and is described below.

As noted earlier, cyclic ester formation is undesirable because this product does not react with polyisocyanates. Consequently, the ultimate urethane polymer will contain cyclic esters, which potentially migrate from the urethane product. This is not acceptable when there will be indirect contact of the urethane with food, for instance.

While teachings in the art suggest that substantial levels (2-3 wt. %) of cyclic esters can be generated in a reaction of phthalic anhydride and ethylene glycol, we found that low cyclic ester contents (<1%) can be achieved when ethylene glycol is used alone or in combination with a polyethylene glycol having a number average molecular weight from 200 to 600 g/mol (see Table 1, below). Moreover, we also found that very low cyclic ester contents can be achieved when PEG-400 is used alone or in combination with EG (see Table 1, Examples 7-9). In contrast, when DEG is used as the diol (Comparative Examples 12-14), the cyclic ester content increases to an unacceptable level (6-8 wt. %).

Polyester polyols made by the inventive method preferably have a number average molecular weight within the range of 500 to 2000 g/mol, more preferably from 500 to 1000 g/mol.

The polyester polyols preferably have a moisture content less than or equal to 0.15%, more preferably less than or equal to 0.05%, as determined by Karl Fisher titration.

The polyols also preferably have Gardner color values less than or equal to 10, more preferably less than or equal to 5.

Preferably, the charged amount of phthalic anhydride (PA) is at least 30 wt. % based on the total amount of phthalic anhydride and diol(s) charged. When the charged amount of PA falls below 30 wt. %, the polyurethane often lacks adequate hardness, tensile properties, or adhesion. More preferably, the charged amount of PA is within the range of 35 to 70 wt. % based on the total amount of PA and diol(s) charged.

In one aspect, the polyester polyol is made in the presence of or is diluted with a natural oil, preferably an oil having hydroxyl functionality. Preferably, the oil is reacted with the polyester polyol to give a transesterified product. Castor oil is a preferred natural oil for this purpose because it occurs naturally with hydroxyl functionality. Other natural oils (soybean oil, linseed oil, or the like) can be used "as is" or can be modified chemically to incorporate hydroxyl groups. Polyester polyols made by the inventive process are frequently viscous, and dilution with castor oil or other natural oils gives formulators a way to reduce viscosity. When a natural oil is used, the relative amounts of polyester polyol and natural oil typically fall within a 1:10 to 10:1 weight ratio, more preferably from 1:2 to 2:1.

Polyester polyols made using the inventive method have utility in a variety of end-use applications, most notably as intermediates for the production of polyurethane rigid foams, coatings, adhesives, sealants, and elastomers. Adhesive formulations include reactive one-component hot-melt products or two-component polyurethanes. In one application, a two-component polyurethane adhesive for flexible packaging is made, and the polyester polyol enables excellent adhesion with reduced tendency of adhesive components to migrate away from the adhesive. Instrument panels based on rigid foams made from polyester polyols of the invention, because of their low cyclic content, should have reduced tendency to fog.

The following examples merely illustrate the invention. Those skilled in the art will recognize many variations that are within the spirit of the invention and scope of the claims.

Analytical Methods

Hydroxyl Value:

An accurately weighed (+/−0.01 g) polyester polyol sample (3-5 g) is combined with 25 mL of standardized acetylating agent (acetic anhydride: 140 mL; water: 3.5 mL; and pyridine: 1 L) in a 250-mL flask equipped with a reflux condenser, and the mixture is heated to reflux for 1-2 h (longer for lower OH values). A blank sample is run the same way without any sample added. Heating is discontinued, and the condensers are rinsed with water (30-50 mL) and then removed. After cooling to room temperature, samples are titrated with standardized 1.000 N KOH solution in the presence of phenolphthalein to a red endpoint, and the volume of titrant required is recorded. Hydroxyl value is calculated as follows.

$$\text{Hydroxyl value (mg KOH/g)} = (A-B)(1.000 \text{ N KOH})(56.1)/\text{g sample, where } A = \text{mL titrant}_{blank} \text{ and } B = \text{mL titrant}_{sample}.$$

Acid value: A polyester polyol sample (3-5 g) is accurately weighed (+/−0.01 g) into a 250-mL titration flask, and acetone (50 mL) is added to dissolve the sample. The mixture is titrated with standardized 0.1000 N KOH solution in the presence of phenolphthalein to a light pink endpoint. Acid value is calculated as follows.

$$\text{Acid value (mg KOH/g)} = (\text{mL titrant}) (5.61)/\text{g sample}$$

Gel Permeation Chromatography (GPC):

Polyester polyol solutions (0.5-1.0 wt. %) in BHT-inhibited tetrahydrofuran (THF) are injected using a Waters 515 HPLC pump and Waters 717 autosampler at 1.00 mL/min. through Phenogel™ (from Phenomenex, Inc.) columns at 35° C. The columns include a 50-mm, 7.8-mm ID linear/mixed guard column, followed by 2×300-mm, 7.8-mm ID (50 Å) columns, followed by a 300-mm, 7.8-mm ID (100 Å) column and a 300-mm, 7.8-mm ID ($10^3$ Å) column. Theoretical plates: 43,000. Detectors: Waters 2410 refractive index detector, Waters 486 tunable UV detector set to 254 nm. Data collection and processing: Empower Pro (2002)/Dell Optiplex GX 280 computer. Calibration: polystyrene standards manufactured by American Polymer Standards Corporation.

The cyclic ester generally elutes in the 37.75 to 39.25-min. region with baseline resolution by UV absorbance detection. Because the cyclic ester peak can coincide with glycol elution when refractive index detection is used, UV-based chromatograms are typically used for integration purposes. (The cyclic esters absorb in the UV region, while the diols do not.)

Examples 1-11 and Comparative Examples 12-14

Polyester polyols are prepared by charging the required amounts (see Table 1) of phthalic anhydride and diol(s) into a 500-mL round-bottom flask equipped with heating mantle, mechanical stirrer, stainless-steel nitrogen sparge tube, thermocouple, temperature controller, and water-cooled condenser. The reactor contents are heated under a slow nitrogen sparge until the contents are clear and a condensate appears (usually around 160° C.). Heating is increased over about three hours and tetra(n-butoxy)titanate (165 ppm based on the total initial charge weight) is added as the temperature of the reaction product approaches 195° C.

The progress of each polyol synthesis is monitored by sampling for acid value. The reaction is judged complete when the acid value falls below 2.0 mg KOH/g. At this time, the hydroxyl value is measured and is corrected to the target amount by adding any necessary glycol. After any hydroxyl value adjustment, products are measured for viscosity and moisture content (0.05% by weight max by Karl Fisher titration). Gel permeation chromatography with an ultraviolet detector is used as described above to measure cyclic ester content.

The "% cyclic" values in Table 1 are area integrations of the GPC UV plots for the cyclic ester region (~38 min.) except for Comparative Examples 12-14, which are weight % values based on comparison with a known sample of the DEG cyclic ester. The % cyclic values in Table 2 are area integrations of the same GPC region using a refractive index (RI) detector.

TABLE 1

Polyester Polyols with Low Cyclic Ester Content

| Ex. # | EG mol % | DEG mol % | PEG-200 mol % | PEG-400 mol % | OHV, mg KOH/g | Viscosity, cP @25° C. | Cyclic, % (UV) | PA wt. % |
|---|---|---|---|---|---|---|---|---|
| 1 | 100 | 0 | 0 | 0 | 56 | >500 K | 1.07 | 67.9 |
| 2 | 100 | 0 | 0 | 0 | 200 | >500 K | 0.16 | 63.1 |
| 3 | 100 | 0 | 0 | 0 | 320 | 33,800 | 0.48 | 59.2 |
| 4 | 0 | 0 | 100 | 0 | 59 | 31,600 | 0.42 | 38.3 |
| 5 | 0 | 0 | 100 | 0 | 218 | 1,100 | 0.48 | 28.8 |
| 6 | 0 | 0 | 100 | 0 | 327 | 276 | 0.53 | 19.1 |
| 7 | 0 | 0 | 0 | 100 | 124 | 972 | 0 | 15.7 |
| 8 | 0 | 0 | 0 | 100 | 203 | 200 | 0 | 7.7 |
| 9 | 50 | 0 | 0 | 50 | 56 | 55,800 | 0 | 34.8 |
| 10 | 50 | 0 | 50 | 0 | 180 | 13,200 | 0.39 | 42.5 |
| 11 | 0 | 0 | 50 | 50 | 173 | 536 | 0.67 | 18.1 |
| C12 | 0 | 100 | 0 | 0 | 53 | >500 K | 7.6* | 55.4 |
| C13 | 0 | 100 | 0 | 0 | 165 | >500 K | 7.7* | 49.7 |
| C14 | 0 | 100 | 0 | 0 | 321 | 2,810 | 5.8* | 41.5 |

"C" denotes a comparative example.
EG = ethlene glycol;
DEG = diethylene glycol;
PEG-number = polyethylene glycol, 200 or 400 nominal molecular weight;
PA = phthalic anhydride.
OHV = hydroxyl value.
Mole percents for DEG, EG & PEGs are for the glycol used only, excluding any PA or catalyst used.
PA wt. % is the amount of charged phthalic anhydride based on the total weight of charged PA and diol(s).
Cyclic % is an area % of the GPC (UV detector) plot for the cyclic ester region (~38 min.) except as noted with an asterisk (*).
*Wt. % values based on comparison with a known sample of the DEG cyclic ester.

TABLE 2

Effect of Ring Size on % Cyclic Esters

| Ex # | Diol | Chain atoms | Ring size | OHV (mg KOH/g) | Cyclic, % (RI) |
|---|---|---|---|---|---|
| 15 | ethylene glycol | 4 | 8 | 320 | 1.0 |
| 16 | 1,3-propanediol | 5 | 9 | 320 | 0.3 |
| C17 | 1,4-butanediol | 6 | 10 | 320 | 2.6 |
| C18 | diethylene glycol | 7 | 11 | 320 | 5.4 |
| 19 | 1,6-hexanediol | 8 | 12 | 320 | 1.2 |
| C20 | triethylene glycol | 10 | 14 | 309 | 3.0 |
| C21 | tripropylene glycol | 10 | 14 | 306 | 3.0 |
| 22 | PEG-200 | 13 | 17 | 320 | <1 |
| 23 | PEG-400 | 26 | 30 | 320 | 0 |

"C" denotes a comparative example.
Ring size presumes a cyclic reaction product of 1 mole of PA and 1 mole of diol.
OHV = hydroxyl value.
Cyclic % is an area % of the GPC (RI detector) plot for the cyclic ester region (~38 min.).

Examples 15, 16, 19, 22, and 23 and Comparative Examples 17, 18, 20, and 21

The procedure of Examples 1-11 is generally followed to prepare polyester polyols having target hydroxyl values in the range of 300-320 mg KOH/g. The diols used are listed in Table 2. Area integrations of the GPC (refractive index detector) plots for the cyclic ester region are used to estimate cyclic ester content.

As shown in the table, cyclic ester contents of about 1% or less are observed with ethylene glycol, 1,3-propanediol, 1,6-hexanediol, PEG-200, and PEG-400, while cyclic ester contents greater than 2% are seen with 1,4-butanediol, diethylene glycol, triethylene glycol, and tripropylene glycol. Thus, there is no clear connection between glycol chain length and the percentage of cyclic esters generated.

The preceding examples are meant only as illustrations; the following claims define the invention.

We claim:

1. A method which comprises reacting phthalic anhydride with a diol selected from the group consisting of propylene glycol, 1,3-propanediol, 2-methyl-1,3-propanediol, neopentyl glycol, polyethylene glycols having a number average molecular weight within the range of 200 g/mol to 600 g/mol, mixtures of ethylene glycol and at least one polyethylene glycol having a number average molecular weight within the range of 200 g/mol to 600 g/mol, and mixtures thereof in the presence of a catalyst comprising titanium at a diol to phthalic anhydride molar ratio within the range of 1.1:1 to 1.6:1 to produce an o-phthalate polyester polyol having a hydroxyl value in the range of 18 to 400 mg KOH/g, an acid value in the range of 0.2 to 5.0 mg KOH/g, and 1 wt. % or less of cyclic esters.

2. The method of claim 1 wherein the molar ratio of ethylene glycol to polyethylene glycol is within the range of 0.2:1 to 3.0:1.

3. The method of claim 1 wherein the polyethylene glycol in said mixtures of ethylene glycol and at least one polyethylene glycol has a number average molecular weight within the range of 250 to 400 g/mol.

4. The method of claim 1 wherein the molar ratio of diol to phthalic anhydride is within the range of 1.1:1 to 1.4:1.

5. The method of claim 1 wherein the polyester polyol has a hydroxyl value within the range of 56 to 320 mg KOH/g.

6. The method of claim 1 wherein the polyester polyol has an acid value within the range of 0.5 to 3.0 mg KOH/g.

7. The method of claim 1 wherein the charged amount of phthalic anhydride is at least 30 wt. % based on the combined amounts of diol and phthalic anhydride.

8. The method of claim 1 wherein the charged amount of phthalic anhydride is within the range of 35 to 70 wt. % based on the combined amounts of diol and phthalic anhydride.

9. The method of claim 1 wherein the polyester polyol has a number average molecular weight within the range of 500 to 2000 g/mol.

10. The method of claim 1 wherein 0.5 wt. % or less of cyclic esters are produced based on the amount of polyester polyol.

11. The method of claim 1 wherein 0.2 wt. % or less of cyclic esters are produced based on the amount of polyester polyol.

12. The method of claim 1 wherein phthalic anhydride and diol are reacted in the presence of a natural oil.

13. A one- or two-component polyurethane adhesive made with a polyester polyol produced by the method of claim 1.

14. A polyurethane coating, sealant, elastomer, flexible foam, or rigid foam made with a polyester polyol produced by the method of claim 1.

* * * * *